(12) United States Patent
Gesswein et al.

(10) Patent No.: US 6,461,383 B1
(45) Date of Patent: Oct. 8, 2002

(54) ULTRASONIC CATHETER VASCULAR STENT SYSTEM AND METHOD (75) Inventors: Douglas H. Gesswein, Temecula, CA (US); Robert C. Esselstein, FallBrook, CA (US); Wayne E. Cornish, FallBrook, CA (US); Leonard D. Barbod, San Diego, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/475,597

(22) Filed: Dec. 30, 1999

(51) Int. Cl.[7] .................................................. A61F 2/06
(52) U.S. Cl. ...................................................... 623/6.11
(58) Field of Search ............................... 623/1.12, 1.11; 606/194, 192, 191, 198, 169; 604/22, 96.01

(56) References Cited

U.S. PATENT DOCUMENTS

| | | | |
|---|---|---|---|
| 5,163,421 A | * 11/1992 | Bernstein et al. ............ 606/159 |
| 5,267,954 A | 12/1993 | Nita .............................. 604/22 |
| 5,368,557 A | 11/1994 | Nita et al. ...................... 604/22 |
| 5,380,274 A | 1/1995 | Nita ............................. 606/169 |
| 5,507,768 A | 4/1996 | Lau et al. .................... 606/198 |
| 5,542,917 A | 8/1996 | Nita et al. ...................... 604/22 |
| 5,569,295 A | 10/1996 | Lam ............................. 606/198 |
| 5,725,494 A | 3/1998 | Brisken ......................... 604/22 |
| 5,728,062 A | 3/1998 | Brisken ......................... 604/22 |
| 5,735,811 A | * 4/1998 | Brisken et al. ................ 604/22 |
| 5,846,218 A | * 12/1998 | Brisken et al. ................ 604/22 |
| 5,916,192 A | 6/1999 | Nita et al. ...................... 604/22 |
| 5,957,882 A | 9/1999 | Nita et al. ...................... 604/22 |
| 6,007,514 A | 12/1999 | Nita .............................. 604/22 |
| 6,296,620 B1 | 10/2001 | Gesswein et al. .............. 604/22 |

* cited by examiner

Primary Examiner—Michael J. Milano
Assistant Examiner—Vy Q. Bui
(74) Attorney, Agent, or Firm—Fulwider Patton Lee & Utecht, LLP (57) ABSTRACT

The invention is directed to a catheter system having an ultrasonic delivery device, a dilatation balloon, and a stent. The ultrasonic distal head is used to ablate a lesion permitting the dilation balloon to cross the lesion for dilatation and for delivering the stent to the lesion. A catheter body includes a first lumen for dilatation balloon expansion control fluid, and a second lumen for the guide wire. The ultrasonic distal head includes a guide wire aperture large enough to permit complete retraction of the guide wire so that the guide wire may be replaced with another while the catheter remains in place within the vasculature of the patient.

17 Claims, 5 Drawing Sheets

ULTRASONIC CATHETER VASCULAR STENT SYSTEM AND METHOD

BACKGROUND

The invention relates generally to a catheter system and method for use in intravascular procedures, and more particularly, to a catheter system that can be positioned in a patient's vasculature to perform ultrasonic ablation, dilatation, and stent insertion.

In typical percutaneous transluminal coronary angioplasty "PTCA" procedures, a guiding catheter having a preformed distal tip is percutaneously introduced into the cardiovascular system of a patient through the brachial or femoral arteries in a conventional Seldinger technique. The catheter is advanced through the arteries until the distal end is in the ostium of the desired coronary artery. A guide wire is positioned within an inner lumen of a dilation catheter and then both are advanced through the guiding catheter to the distal end thereof. The guide wire is first advanced out of the distal end of the guiding catheter into the patient's coronary vasculature until the distal end of the guide wire crosses a lesion to be dilated, then the dilation catheter having an inflatable balloon on the distal portion thereof is advanced into the patient's coronary anatomy over the previously introduced guide wire until the balloon of the dilation catheter is properly positioned across the lesion. Once in position across the lesion, the balloon, which is made of relatively inelastic materials, is inflated to a predetermined size with radiopaque liquid at relatively high pressure (e.g., greater than 4 atmospheres) to compress the arteriosclerotic plaque of the lesion against the inside of the artery wall and to otherwise expand the inner lumen of the artery. The balloon is then deflated so that blood flow can be resumed through the dilated artery and the dilation catheter can be removed therefrom. Further details of dilation catheters, guide wires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson et al.); U.S. Pat. No. 4,554,929 (Samson et al.); U.S. Pat. No. 4,616,652 (Simpson); (U.S. Pat. No. 4,638,805 (Powell); and U.S. Pat. No. 4,748,982 (Horzewski et al.).

A major problem which can occur during balloon angioplasty procedures is the formation of intimal flaps which can collapse and occlude the artery when the balloon is deflated at the end of the angioplasty procedure. Another major problem characteristic of balloon angioplasty procedures is the large number of patients subject to re-stenosis in the treated artery. In the case of re-stenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient is put in a dangerous situation requiring immediate medical attention, particularly in the coronary arteries.

A major focus of recent development work in the treatment of heart disease has been directed to endoprosthetic devices called stents. Stents are generally cylindrically shaped intravascular devices which are placed within a damaged artery to hold it open. The device can be used to prevent re-stenosis and to maintain the patency of a blood vessel immediately after intravascular treatments. In some circumstances, they can also be used as the primary treatment device where they are expected to dilate a stenosis and then are left in place.

Devices and methods for the rapid and effective delivery of a stent to the desired location within the patient's vasculature have been developed. Two basic methods and systems have been developed for delivering stents to desired locations within body lumina. One method and system involves compressing or otherwise reducing the diameter of an expandable stent, disposing the compressed stent within a lumen provided in the distal end of a tubular catheter, advancing the catheter through the patient's vasculature until the distal end of the catheter is immediately adjacent the desired vascular location, and then pushing the stent out the distal end of the catheter into the desired location. Once out of the catheter, the compressed stent expands or is expanded to thereby hold open the artery or other body lumen into which it is placed. The stent is left in the artery, either temporarily or permanently, at the site of a dilated lesion.

The following references illustrate various types of stents and stent delivery systems. The list is meant to be exemplary, not exhaustive on the subject.

| | |
|---|---|
| U.S. Pat. No. 3,868,956 | U.S. Pat. No. 4,795,458 |
| U.S. Pat. No. 4,503,569 | U.S. Pat. No. 4,800,882 |
| U.S. Pat. No. 4,512,338 | U.S. Pat. No. 4,830,003 |
| U.S. Pat. No. 4,553,545 | U.S. Pat. No. 4,856,516 |
| U.S. Pat. No. 4,560,374 | U.S. Pat. No. 4,878,906 |
| U.S. Pat. No. 4,655,771 | U.S. Pat. No. 4,886,062 |
| U.S. Pat. No. 4,665,918 | U.S. Pat. No. 4,907,336 |
| U.S. Pat. No. 4,733,665 | U.S. Pat. No. 4,913,141 |
| U.S. Pat. No. 4,760,849 | U.S. Pat. No. 4,923,464 |
| U.S. Pat. No. 4,762,128 | U.S. Pat. No. 4,950,227 |
| U.S. Pat. No. 4,768,507 | |

However, in some cases it has been found that the above methods cannot be performed. For example, where the target lesion is distal to a 50% or greater stenosis that cannot be pre-dilated, or a target lesion is located proximal to untreatable areas of significant flow compromising disease, the above methods have been unusable. As another example, the above methods have little application where there exists a resistant lesion (fibrotic or calcific) that cannot be pre-dilated. In such a case, the lesion would be resistant to complete balloon inflation at 20 atmospheres. In yet another example, the above methods have had limited or no value in patients judged to have a lesion that prevents complete inflation of an angioplasty balloon.

It has been known that ultrasonic energy may be applied to occlusions to ablate particularly difficult occlusive material from a body lumen thereby opening a larger lumen for later use with a dilatation balloon. However, this approach involves threading at least two catheters through the vascular system of the patient, prolonging the procedure, and providing more trauma to the patient.

In the use of ultrasonic ablation catheters, often multiple lesions will be treated within a single operation. This requires that the guide wire and catheter be repeatedly advanced through narrower and more tortuous arteries. This may require exchanging the guide wire for one or more guide wires appropriate to the new location, or reshaping the distal tip of the existing guide wire before continuing with the procedures.

Exchanging the guide wire in previous catheter designs poses difficulties. The entire therapeutic catheter must be withdrawn, which is difficult and time consuming, requiring reinserting the assembly back to its original location. Previous methods of removing the guide wire while leaving the catheter in place require reinserting the wire along side the catheter and inserting the guide wire into a side port in the assembly. While effective, this also can be time consuming and difficult.

Hence, those skilled in the art have recognized a need for an apparatus and method that can apply ultrasonic energy, dilatation, and a stent with a single device to reduce trauma to a patient. Additionally, a need has been recognized for a device and method that can overcome the above examples of occlusions that prevent the application of dilatation and stent devices so that treatment is possible. In particular, it would be of value to provide a system and method to pre-treat such occlusion examples so that a lower pressure dilatation balloon may be used for dilation prior to placement of a stent device. Additionally, those skilled in the art have also recognized a need for a catheter system and method that can pre-treat occlusions readying them for dilatation devices while at the same time, reducing the trauma to a patient's vascular system. In conjunction with this need, what has also been heretofore unavailable is an intraluminal lesion removal catheter that provides for the easy and rapid exchange of the guide wire. The invention addresses these needs and others.

SUMMARY OF THE INVENTION

Briefly and in general terms, the invention is directed to a medical catheter system for recanalization of a tubular anatomical structure, such as a blood vessel, the catheter system comprising an elongate flexible catheter body having a distal end and a proximal end, an ultrasonic delivery device mounted at the distal end of the catheter body, a dilatation balloon mounted at the distal end of the catheter body, a stent mounted at the distal end of the catheter body such that it may be delivered to the tubular anatomical structure by the distal end of the catheter body, a first lumen disposed longitudinally within the catheter body extending from the proximal end to the distal end and in fluid communication with the dilatation balloon for conducting expansion control fluid to the balloon, and an ultrasound transmission member extending longitudinally through the catheter body from the proximal end and mounted to the ultrasonic delivery device, the transmission member configured to transfer ultrasonic energy to the ultrasonic delivery device.

In more detailed aspects, the ultrasonic delivery device comprises a distal head rigidly mounted to the distal end of the catheter body such that longitudinal and radial movement of the distal head only occurs with like movement of the distal end of the catheter body. The catheter system further comprises a second lumen disposed longitudinally within the catheter body extending from the proximal end to the distal end, the second lumen having a size large enough to accept a guide wire extending into the catheter from the proximal end of the catheter body and to permit the extension of the guide wire distally beyond the distal end, whereby a guide wire may be entirely removed from the catheter body and replaced by another guide wire without removing the catheter from the anatomical structure.

In yet further aspects, the ultrasonic delivery device comprises a guide wire aperture extending completely through the distal head through which the guide wire may be located, the aperture having a size large enough so that the guide wire may be completely retracted through the distal head so that the guide wire may be exchanged with another. The stent is mounted to the outside surface of the balloon such that expansion of the balloon into contact with the tubular anatomical structure delivers the stent into a selected location at the tubular anatomical structure. The catheter system further comprises a radiopaque marker disposed at a selected location on the catheter body. Further, the catheter system also comprises a protective sheath disposed over the stent and the dilatation balloon, the sheath being movable in an axial direction to selectively uncover the stent to allow delivery of the stent to the tubular anatomical structure.

In other aspects, the catheter body includes a guide wire port formed in the catheter body at a location between the proximal and distal ends for locating a guide wire. The catheter system further comprises a second lumen disposed longitudinally within the catheter body extending from the proximal end to the distal end, the second lumen having a size large enough to accept a guide wire extending into the catheter from the proximal end of the catheter body and to permit the extension of a guide wire distally beyond the distal end of the catheter wherein the ultrasonic delivery device comprises a distal head rigidly mounted to the distal end of the catheter body such that longitudinal and radial movement of the distal head is not possible without like movement of the distal end of the catheter body, the distal head having a guide wire aperture aligned with the second lumen, the aperture having a size large enough so that the guide wire may be completely retracted through the distal head so that the guide wire may be exchanged with another, whereby a guide wire may be entirely removed from the catheter body and replaced by another guide wire without removing the catheter from the anatomical structure.

In more detailed aspects of a method, the method for recanalization of a tubular anatomical structure, such as a blood vessel, comprises the steps of advancing an elongate flexible catheter body having a distal end and a proximal end to a lesion in the tubular anatomical structure, applying ultrasonic energy to the lesion with the distal end of the catheter body to ablate the lesion, crossing the lesion with a guide wire, crossing the lesion with a dilatation balloon mounted at the distal end of the catheter body, dilating the lesion with the dilatation balloon, delivering a stent to the dilated lesion from the distal end of the catheter body, and withdrawing the catheter from the tubular anatomical structure.

In further detailed method aspects, the method further comprises the steps of removing a first guide wire from the catheter body while retaining the catheter body in place in the tubular anatomical structure, and inserting a second guide wire through the catheter body while it remains in place in the tubular anatomical structure. The method further comprises the step of delivering the stent to the lesion at the same time that the balloon is expanded to dilate the lesion. And yet further, the step of applying ultrasonic energy comprises the step of applying ultrasonic energy with a distal head rigidly mounted at the distal end of the catheter body, the distal head mounted such that longitudinal and radial movement of the distal head occurs only with like movement of the distal end of the catheter body.

These and other aspects, objects, and advantages of the invention will become apparent to those skilled in the art from the following detailed description in conjunction with the accompanying drawings.

DETAILED DESCRIPTION OF THE PREFERRED EMBODIMENTS

Figure 1:
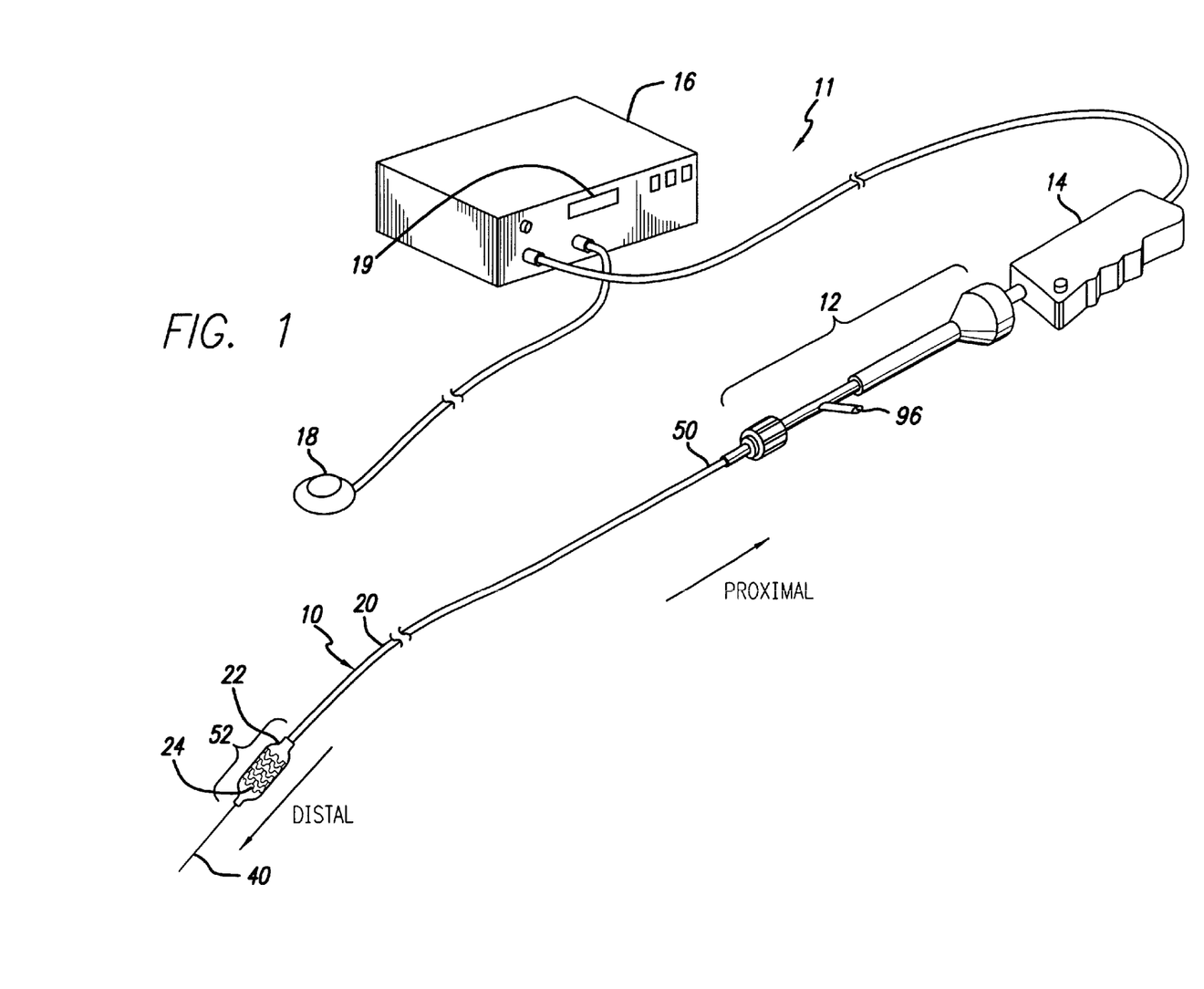
FIG. 1 is a view of an ultrasonic energy delivery system including a dilatation catheter with a stent and an ultrasonic wire, an ultrasonic transducer, a generator, and a foot switch to control the application of ultrasonic energy to a patient.

Turning now to the drawings, in which like numerals indicate like or identical elements among the drawings, there is illustrated in FIG. 1 an ultrasonic catheter vascular stent system 10 embodying features of the invention. The catheter system 10 generally comprises an elongated tube or catheter body 20 with multiple continuous lumina. In a first lumen, an ultrasound transmission member may be located, while a guide wire may be located in a second lumen, and balloon expansion control fluid located in a third lumen.

The perspective view in FIG. 1 is of an over-the-wire ultrasound catheter stent system 10 in accordance with principles of the present invention, having a proximal end connector assembly 12 mounted on the proximal end thereof. As used herein, the term "over-the-wire" shall refer to a catheter that has a guide wire passage lumen formed within the body of the catheter such that a flexible guide wire may be advanced through the body of the catheter and out of a guide wire passage aperture formed in the distal end of the catheter. Returning to FIG. 1, an ultrasound transducer 14 is connected to the proximal end of the proximal connector assembly 12. An ultrasound generator 16 having a foot-actuated on/off switch 18 is operatively connected to the ultrasound generator 14 so as to send ultrasonic energy through the ultrasound catheter 10, when desired. The ultrasound generator 16 includes a front panel display 19 for indicating various information concerning the application of energy. The distal end of the catheter includes a dilatation balloon 22 and a stent 24 and is configured to be percutaneously inserted into a body vascular system and through tortuous body lumina to a desired location within the body vascular system.

Figure 2:
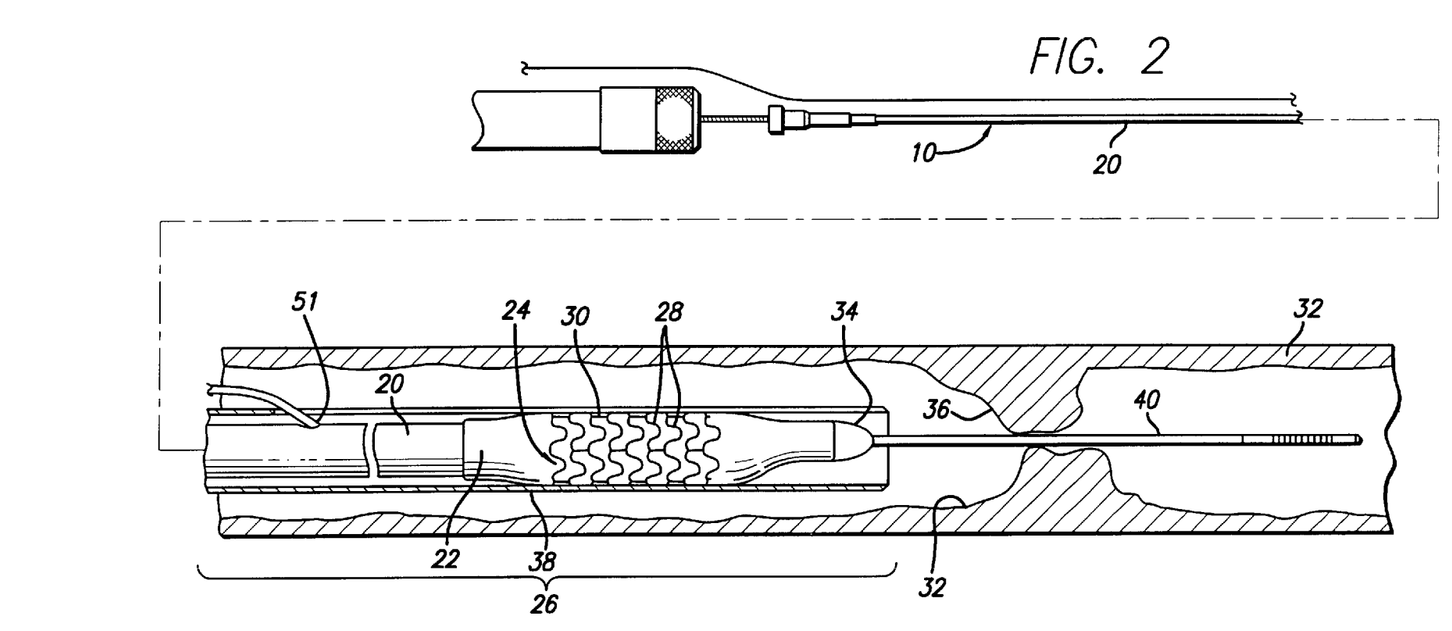
FIG. 2 is a more detailed view of a catheter system in accordance with aspects of the present invention showing in larger form, the distal end of the catheter having an ultrasonic delivery device, a dilatation balloon, and an expandable stent.

FIG. 2 provides a more detailed view of a catheter system in accordance with aspects of the invention. In particular, a stent 24 is mounted on a dilatation balloon 22 located at the distal end 26 of a delivery catheter 10. The stent generally comprises a plurality of radially expandable cylindrical elements 28 disposed generally coaxially and interconnected by members 30 disposed between adjacent cylindrical elements. The expandable portion or balloon 22 of the catheter 10 is used to dilate a lesion as well as expand the stent within an artery 32 or other tubular anatomical structure. The distal end 26 of the catheter 10 includes an ultrasonic delivery device 34 that is used to impart ablative ultrasonic energy to material with which it comes in contact. The artery 32 as shown in FIG. 2, has a lesion 36 that has occluded a substantial portion of the arterial passageway.

The delivery catheter 10 onto which the stent 24 is mounted, is essentially the same as a conventional balloon dilatation catheter for angioplasty procedures except that it also includes an ultrasonic energy delivery device 34, described in further detail below. The balloon 22 may be formed of suitable materials such as polyethylene, polyethylene terephthalate, polyvinyl chloride, nylon, co-polyamide such as PEBAX manufactured by Elf Atochem, or ionomers such as Surlyn manufactured by the Polymer Products Division of the Du Pont Company. Other polymers may also be used. In order for the stent 24 to remain in place on the balloon 22 during delivery to the site of the damage within the artery 32, the stent 24 is compressed onto the balloon. A retractable protective delivery sleeve 38 may be provided to further ensure that the stent stays in place on the expandable portion of the delivery catheter 10 and prevent abrasion of the body lumen by the open surface of the stent 24 during delivery to the desired arterial location. Other means for securing the stent onto the balloon may also be used, such as providing collars or ridges on the ends of the working portion, i.e., the cylindrical portion, of the balloon.

Each radially expandable cylindrical element 28 of the stent 24 may be independently expanded, therefore the balloon 22 may be provided with an inflated shape other than cylindrical, e.g., tapered, to facilitate implantation of the stent 24 in a variety of body lumen shapes.

Figure 3:
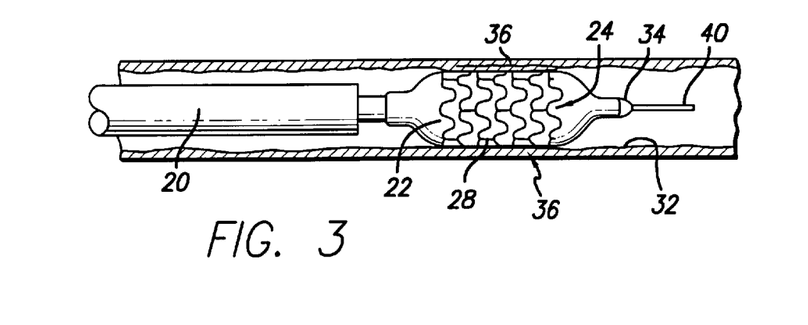
FIG. 3 presents a view of the dilatation balloon delivering the stent to a damaged vessel wall.

In a preferred embodiment, the delivery of the stent is accomplished in the following manner. The stent 24 is first mounted onto the inflatable balloon 22 on the distal end of the delivery catheter 26. The stent may be "crimped" down onto the balloon to obtain a low profile. The catheter-stent assembly can be introduced within the patient's vasculature in a conventional Seldinger technique through a guiding catheter (not shown). A guide wire 40 is disposed across the damaged arterial section with the occlusion 36. The ultrasonic device 34 is applied to the occlusion 36 to ablate a passageway large enough for the balloon/stent combination to be located across the occlusion. The catheter-stent assembly is advanced over the guide wire 40 within the artery 32 until the stent 24 is directly across the occlusion 36. The balloon of the catheter is expanded, expanding the stent against the artery, which is illustrated in FIG. 3. While not shown in the drawing, the artery 32 is preferably expanded slightly by the expansion of the stent to seat or otherwise fix the stent and prevent movement. In some circumstances during the treatment of stenotic portions of an artery, the artery may have to be expanded considerably in order to facilitate passage of blood or other fluid therethrough.

Figure 4:
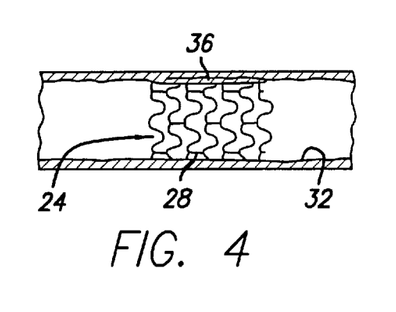
FIG. 4 shows the delivered stent in place maintaining the patency of the blood vessel of a patient.

The stent 24 serves to hold open the artery after the catheter is withdrawn, as illustrated by FIG. 4. Due to the formation of the stent from an elongated tubular member, the undulating component of the cylindrical elements of the stent is relatively flat in transverse cross-section, so that when the stent is expanded, the cylindrical elements are pressed into the wall of the artery and as a result do not interfere with the blood flow through the artery. The cylindrical elements 28 of the stent which are pressed into the wall of the artery will eventually be covered with endothelial cell growth which further minimizes blood flow interference. The serpentine pattern of the cylindrical sections provide good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery.

Prior art stent designs, such as the MultiLink Stent™ manufactured by Advanced Cardiovascular Systems, Inc., Santa Clara, Cal., include a plurality of cylindrical rings that are connected by three connecting members between adjacent cylindrical rings. Each of the cylindrical rings is formed of a repeating pattern of U-, Y-, and W-shaped members, typically having three repeating patterns forming each cylindrical ring. A more detailed discussion of the configuration of the MultiLink Stent™ can be found in U.S. Pat. No. 5,569,295 (Lam) and U.S. Pat. No. 5,514,154 (Lau et al.).

While FIGS. 1–4 depict a stent being used to treat a vessel having an occlusion 36 a stent 24 can be used for purposes other than repairing a lining. Those other purposes include, for example, supporting the vessel, reducing the likelihood of re-stenosis, or assisting in the attachment of a vascular graft (not shown) when repairing an aortic abdominal aneurysm.

Figure 5:
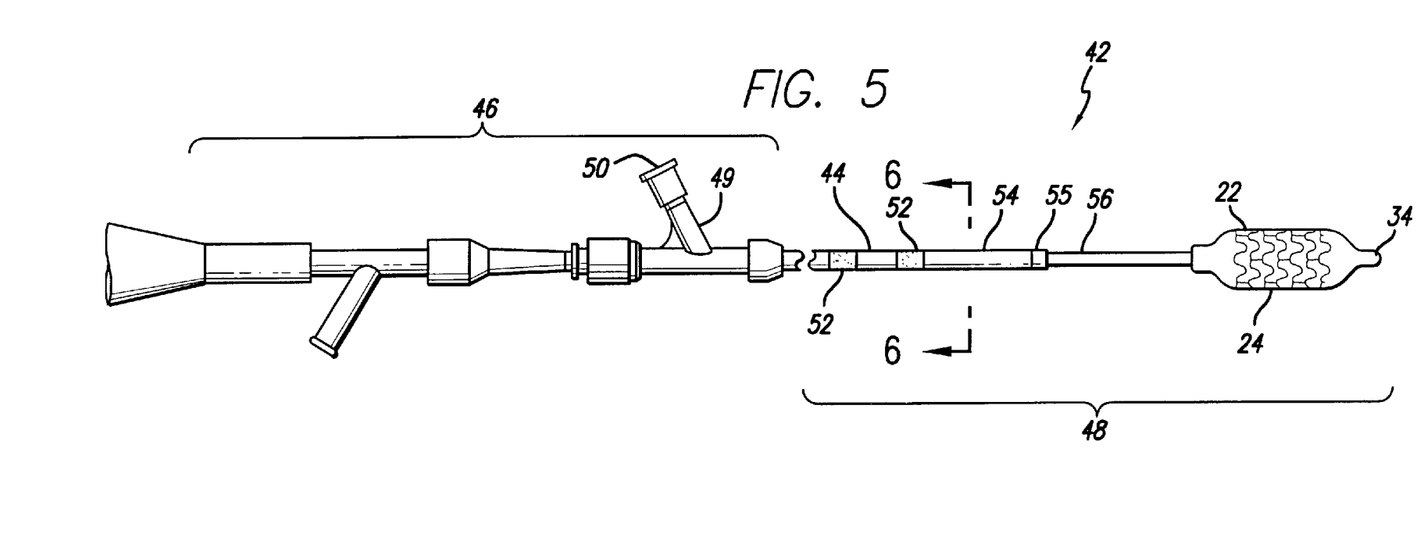
FIG. 5 is another view of a catheter system incorporating principles of the present invention, including multiple tubes forming the catheter body.

Referring now to FIG. 5, there is shown another view of a catheter system incorporating principles of the present invention. A more detailed view of different aspects of a catheter is shown. In particular, this catheter 42 includes an elongate body 44, a proximal end 46, and a distal end 48. At the proximal end are shown an adaption arm 49 and access port 50. A dilatation balloon 22 is mounted at the distal end 48 with an associated stent 24. The stent 24 is located on the outer surface of the balloon so that balloon expansion will cause the stent to expand as well. The balloon is designed to deliver an expandable stent of known diameter and length at specified pressures. Also located at the distal end 48 is an ultrasonic delivery device 34. Located between the proximal 46 and distal 48 ends are radiopaque markers 52. These are positioned on the catheter body 44 to assist in accurate positioning of the stent/balloon in the artery. The markers help the physician gauge the dilatation catheter position relative to the guiding catheter tip.

The catheter body 44 in FIG. 5 comprises two tubes, a proximal tube 54 and a distal tube 56. The two tubes are joined together 55 in the distal end 48. As shown, the distal tube 56 is of a smaller diameter than the proximal tube 54 to achieve greater flexibility for use in smaller vessels. The two tubes may be connected together by means well known to those skilled in the art, such as by ultrasonic welding, adhesive, or other means. Further, the distal tube 56 of the catheter may be coated with a lubricious coating.

Figure 6:
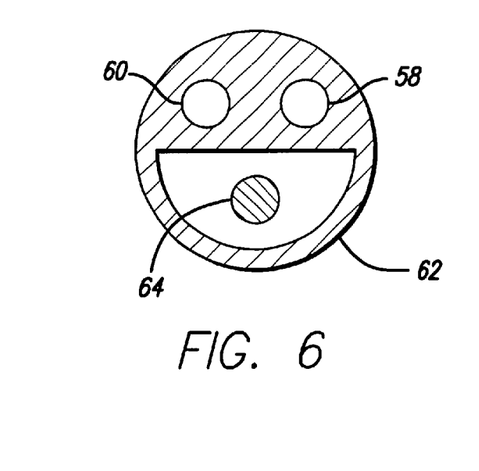
FIG. 6 is a cross-sectional view of a portion of FIG. 5.

The catheter body 44 of FIG. 5 may be constructed of multiple lumina. Turning now to FIG. 6, there is shown a cross section of FIG. 5 along lines 6—6 of FIG. 5. The first lumen 58 may provide a reservoir for balloon inflation via contrast medium, the second lumen 60 may permit use of a guide wire to facilitate advancement of the catheter to vessel lesions, and the third lumen 62 may provide a channel for the ultrasound wire 64 and for irrigation or cooling fluid.

Referring again to FIG. 5, the adaption arm 49 on the proximal end 46 of the catheter body 44 provides access to the inflation and irrigation lumina. The side arm 50 inflation lumen access port is designed with a Luer-lock fitting to facilitate connection to an inflation device.

The catheter shown in FIG. 2 is a rapid exchange type catheter with the guide wire entering the catheter body at a point 51 between the proximal and distal ends.

Figure 7:
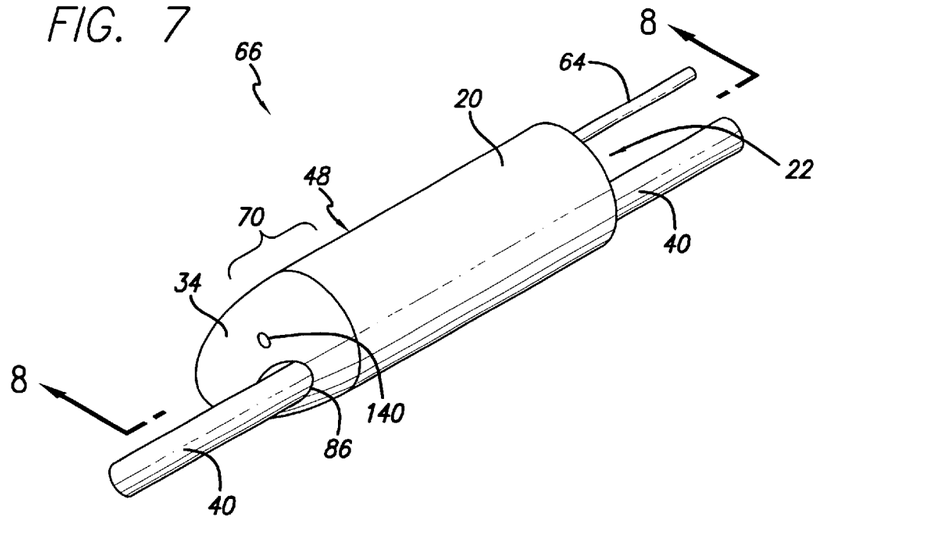
FIG. 7 is a perspective view of a portion of the distal end of a catheter in accordance with aspects of the invention, showing the protrusion of a guide wire through the distal head, and also showing that the catheter body contains an ultrasound conduction wire and a guide wire.
Figure 8:
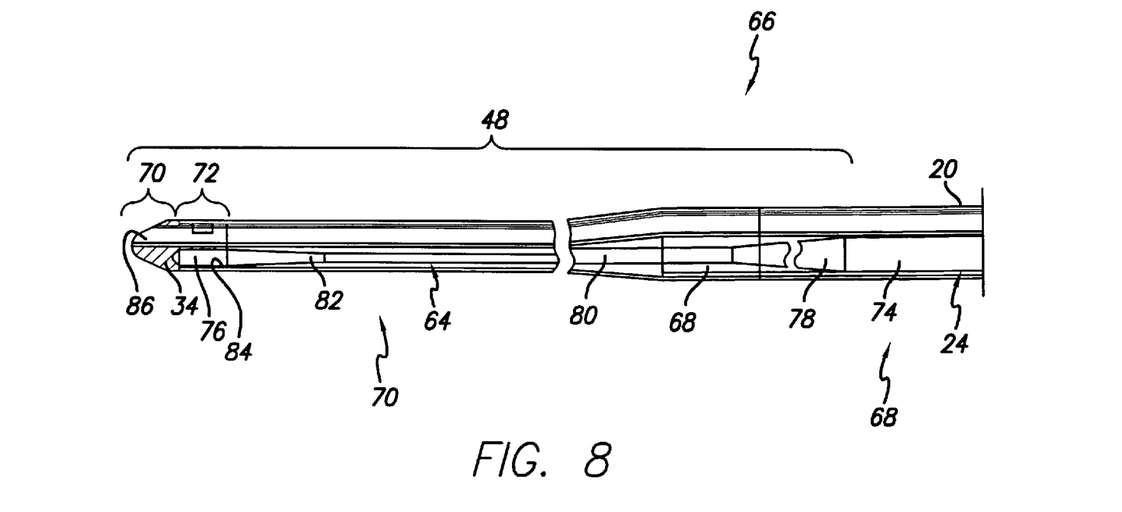
FIG. 8 shows a cross-sectional view of FIG. 7 with details of the ultrasound conduction wire, the distal head, and the guide wire lumen.

One embodiment of an over-the-wire ultrasound catheter 66 in accordance with the present invention is shown in more detail in FIGS. 7 and 8. An over-the-wire ultrasound catheter 66 in accordance with the present invention comprises a flexible, elongate, tubular catheter body 20 having a hollow lumen extending longitudinally therethrough. The catheter body defines at least two internal lumina with the first lumen configured to house a means of transmitting ultrasonic energy from outside the body vascular system, into the proximal end of the catheter body, through the entire length of the catheter body, to the ultrasound delivery device 34. The figures illustrate an ultrasound transmission member or wire 64 extending throughout the first inner lumen and attached to an ultrasonic tip or distal head 34 at the distal end 48 of the elongated tube. In the over-the-wire embodiment of FIGS. 7 and 8, the ultrasound transmission member 64 extends longitudinally through the lumen 68 of the catheter body to transmit ultrasonic energy generated by the ultrasound transducer 14 connected to the proximal end 12 of the catheter 66 to the distal end 48 of the catheter 66.

A second inner lumen is configured to house a guide wire 40 extending from outside the patient's vasculature, into the proximal end 12 of the catheter body 66, through the entire length of the body, to a point beyond the distal end 48 of the catheter body and beyond the distal head 34. Furthermore the second inner lumen is configured to allow the guide wire to be, extended and retracted throughout the entire length of the tube without removing the catheter from the patient's vasculature. These uses require the second inner lumen to be continuous throughout the entire length of the tube.

Preferably a distal head 34 is mounted on the distal end of the ultrasound transmission member 64. In the embodiment shown, the distal head 34 comprises a generally round, conical, or disc-shaped distal portion 70 and a reduced diameter neck portion or proximal portion 72. The outer diameter "OD" of the proximal portion 72 of the distal head 34 is approximately the same as or slightly less than the inner diameter "ID" of the catheter lumen such that the proximal portion 72 of the distal head may be inserted into the distal end of the lumen, to a point where the distal end of the catheter body abuts against the proximal aspect of the distal portion 70 of the distal head, as shown in FIGS. 7 and 8.

The ultrasound transmission member 64 may be formed of any material capable of effectively transmitting the ultrasonic energy generated by the ultrasound transducer 14 to the distal head 34 of the catheter body 20, including but not necessary limited to metal, plastic, hard rubber, ceramic, and/or composites thereof. In accordance with one aspect of the invention, all or a portion of the ultrasound transmission member 64 may be formed of one or more materials which exhibit super elasticity. Such material(s) should preferably exhibit super elasticity consistently within the range of temperatures normally encountered by the ultrasound transmission member 64 during operation of the catheter 66. Specifically, all or part of the ultrasound transmission member 64 may be formed of one or more metal alloys known as "shape memory alloys."

Examples of super elastic metal alloys that are usable to form the ultrasound transmission member 64 in the embodiment shown are described in detail in U.S. Pat. Nos. 4,665, 906 (Jervis); 4,565,589 (Harrison); 4,505,767 (Quin); and 4,337,090 (Harrison). In particular, one presently preferred super elastic metal alloy of which the ultrasound transmission member 64 may be formed is a nickel-titanium alloy wire made up of 55.8 weight percent nickel (NiTi containing 55.8% weight % Ni with the balance formed of Ti). Such material is commercially available at Tinel™ Wire from Raychem Corporation, Menlo Park, Calif.

The ultrasound transmission member 64 may be tapered, narrowed, or otherwise reduced in cross-sectional dimension within a distal portion of the catheter so as to decrease the rigidity of the ultrasound transmission member within such distal portion and also to cause amplification of the ultrasound energy transmitted to the distal head. As shown in FIG. 8, such tapering or narrowing of the ultrasound transmission member divides the ultrasound transmission member into a proximal portion 74 and a distal portion 76. An angular tapered or narrowing region 78 embodies a transition zone between the larger proximal portion 74 and a reduced diameter distal portion 80. Because the reduced diameter distal portion 80 of the ultrasound transmission member is of smaller cross-sectional diameter and less mass, it is more flexible and less rigid than the proximal portion 74 thereof. Such configuration of the ultrasound member enables the relatively large sized proximal portion to transmit more ultrasonic energy than if the entire length of the ultrasound transmission member were of the relatively small cross-sectional size of the reduced diameter distal portion thereof. Additionally, such decrease in the cross-sectional size of the reduced diameter distal portion of the ultrasound transmission member results in an amplification of the ultrasound energy transmitted through such reduced diameter distal portion thereof. Thus, by limiting the reduced diameter distal portion of the ultrasound transmission member 64 to a discrete region at the distal end 48 of the catheter 66, the proximal portion of the ultrasound transmission member is rendered capable of transmitting a greater amount of ultrasonic energy to the distal end of the catheter than would otherwise be possible while the reduced diameter distal portion of the ultrasound transmission member additionally serves to amplify the ultrasound energy reaching the distal head 34 of the device.

In the embodiment of the catheter 66 shown in FIG. 8, the outer diameter of the distal portion 48 of the catheter is also reduced to coincide with the reduced diameter distal portion 80 of the ultrasonic transmission member, and also will exhibit less rigidity and greater flexibility than the remainder of the catheter body.

The present embodiment further includes an optional improvement to the ultrasound transmission member 64, said improvement comprising the disposition of a low friction coating or jacket on the outer surface of all or a portion of the ultrasound transmission member. The low friction coating or jacket may be disposed on the outer surface of the ultrasound transmission member so as to completely cover the ultrasound transmission member along its entire length, or along a discrete region or regions thereof. Such coating or jacket may comprise a layer of low friction polymer material such as polytetrafluoroethylene (ptfe) (Teflon™ Dupont, Inc., Wilmington, Del. ) or other plastic materials such as polyethylene. The coating or jacket may be applied as a liquid and subsequently allowed to cure or harden on the surface of the ultrasound transmission member. Alternatively, the coating or jacket may be in the form of an elongate tube slidably disposable over the outer surface of the ultrasound transmission member. Such coating or jacket serves to prevent or diminish friction between the outer surface of the ultrasound transmission member and the adjacent structures of the catheter 66 or proximal end connector assembly 12 through which the ultrasound transmission member extends.

The distal head 34 is firmly bonded, attached, or connected to the catheter body 20 such that the distal head is prevented from undergoing longitudinal or transverse movement separate from or relative to the catheter body. Additionally, such affixation of the distal head to the catheter body increases the conveyance of ultrasound energy into the distal portion of the catheter body 20, thereby resulting in enhanced cavitation effects created by the distal portion of the catheter body. Such bonding connection or attachment of the distal head 34 to the catheter body may be accomplished by any suitable means. One means of attaching the distal head 34 to the catheter body 20 is through the use of an adhesive.

In the embodiments shown in FIGS. 7 and 8, the adhesive is applied to the neck portion 72 of the distal head 34 prior to insertion thereof into the distal end of the lumen of the catheter body 20. The adhesive may comprise any suitable adhesive, such as cyanoacrylate (e.g. Loctite™, Loctite Corp., Ontario, CANADA or Dron Alpha™, Borden, Inc., Columbus, OH) or polyurethane (e.g. Dymax™ , Dymax Engineering Adhesive, Torrington, CN) to firmly bond and attach the distal head 34 to the catheter body 20. The distal head 34 may be formed of any suitable rigid material such as metal or plastic. In devices wherein the distal head is formed of plastic, the surrounding plastic catheter body 20 may be thoroughly welded, heat sealed, or solvent welded to the plastic distal head 34, in accordance with the types of plastics employed.

In the alternative to the use of adhesives, various mechanical or frictional connectors, such as screw threads, lugs or other surface modifications formed on the proximal portion 72 of the distal head 34, may be utilized to hold the distal head in a fixed position relative to the catheter body 20. In such embodiments, corresponding grooves, detents, or surface modifications may also be formed in the surrounding inner wall of the catheter body so as to cooperate with any such threads, lugs or other surface modifications formed on the opposing surface of the distal head. Such threads, lugs or other surface modifications will be configured and constructed so as to mechanically or frictionally hold the distal head in fixed position relative to the catheter body 20.

The distal head is preferably formed of radio dense material so as to be easily discernable by radiographic means. Accordingly, the distal head may preferably be formed of metal or, alternatively, may be formed of plastic, ceramic or rubber materials, optionally having one or more radio dense markers fixed thereto or formed therein. For example, the distal head may be molded of plastic such as acrylonitrile-butadiene-styrene (ABS) and one or more metallic foil strips or other radio opaque markers may be affixed to such plastic distal head in order to impart sufficient radio density to permit the distal head to be readily located by radiographic means. Additionally, in embodiments wherein the distal head is formed of molded plastic or other non-metallic material, a quantity of radio dense filler such as powdered bismuth or $BaSO_4$ may be disposed within the plastic or other non-metallic material of which the distal head is formed so as to impart enhanced radio density to the distal head.

Referring specifically to FIG. 8, the ultrasound transmission member 64 is tapered outward 82 at its most distal extreme 76 to a size that fits within a cavity 84 formed in the distal head 34. Although this outward taper attenuates the ultrasonic energy somewhat, it results in a greater surface area for improved attachment to the distal head 34.

The second or guide wire lumen is continuous throughout the entire length of the catheter body 20 and is larger than the largest guide wire used so as to permit cooling fluid or irrigation fluid to be introduced to the catheter and flow out of the guide wire passage aperture 86 at the distal head of the catheter. The provision of such fluid outflow at the distal end of the catheter facilitates continual or intermittent passage of coolant liquid through the distal head. Although the lumen 58 used for fluid outflow is not the same lumen in which the ultrasound transmission member is located, the lumen 58 is through the distal head which provides the cavitation forces against occlusive material and is therefore likely to develop heat. The coolant liquid may be infused into the proximal end of the lumen, through the lumen, and may exit through the guide wire passage aperture 86 in the distal head 34 in a manner that will bathe and cool the distal head. Additionally, the guide wire lumen is next to the ultrasound transmission member 64 and will carry away a significant amount of heat generated by the ultrasound transmission member thereby preventing the ultrasound transmission member from overheating during use.

The guide wire passage aperture 86 extends longitudinally through the distal head 34. Such guide wire passage aperture 86 may be formed through the distal head at a location inboard of the catheter body 20 such that a guide wire 40 may be advanced through the lumen of the catheter body 20 and through the guide wire passage aperture 86. This embodiment of the ultrasound catheter 10 in which the guide wire 40 passes through a lumen formed within the catheter body 20 and out of the catheter passage aperture 86 constitutes an "over-the-wire" embodiment of the invention. In this embodiment, a guide wire lumen is disposed within substantially the entire length of the catheter body from the proximal connector assembly 12 at the proximal end 46 of the catheter body 20 through the distal head 34 at the distal end 48.

The elongated catheter body 20 is formed by conventional techniques, e.g. extruding from materials already found useful in intravascular catheters such as polyethylene, polyamide, polyvinyl chloride, polyesters and composite materials such as described in U.S. Pat. No. 4,981,478 (Evard et al.). The various members of the catheter are joined by suitable adhesives such as the cyanoacrylate based adhesive sold as LOCTITE™ 405. Heat shrinking may also be employed where appropriate.

The size of the catheter body 20 and the second inner lumen, housing the guide wire, are, to a large extent, determined by the size of the guide wires to be employed and the size of the artery or other body lumen through which the catheter must pass. Generally the diameter of the second inner lumen is sufficient to accommodate the guide wire and to allow it to be slidably disposed therein. The diameters of the guide wires for coronary use vary from about 0.008 to about 0.014 inches (0.2–0.36 mm) in diameter, and the inner diameter of the second lumen should be larger than the guide wire diameter by about 0.001 to 0.005 inches (0.025–0.127 mm) than the largest diameter guide wire to be used with the catheter 10. The catheter body 20 is sufficiently long to extend from outside the proximal end of a guiding catheter, which likewise extends out of the patient, to a lesion to be treated within the patient's vascular system (or other desired location therein) e.g. from about 100 cm to about 150 cm when a Seldinger approach through the femoral artery is employed to introduce the catheter into the body vascular system. The wall forming the catheter must be of sufficient thickness and strength so that it can be pushed over the guide wire to the desired location within the patient's blood vessel. If desired the proximal portion of the catheter shaft may be provided with a stiffening means to facilitate the advancement of the catheter within the body vascular system. This over-the-wire catheter body preferably has an outside diameter within the range of 0.5 mm to 5.0 mm. In catheters intended for insertion into tortuous or relatively small anatomical structures (e.g., the coronary arteries), it is preferable that the outer diameter of the catheter body 20 be within the range of 0.25 mm to 2.5 mm.

Figure 9:
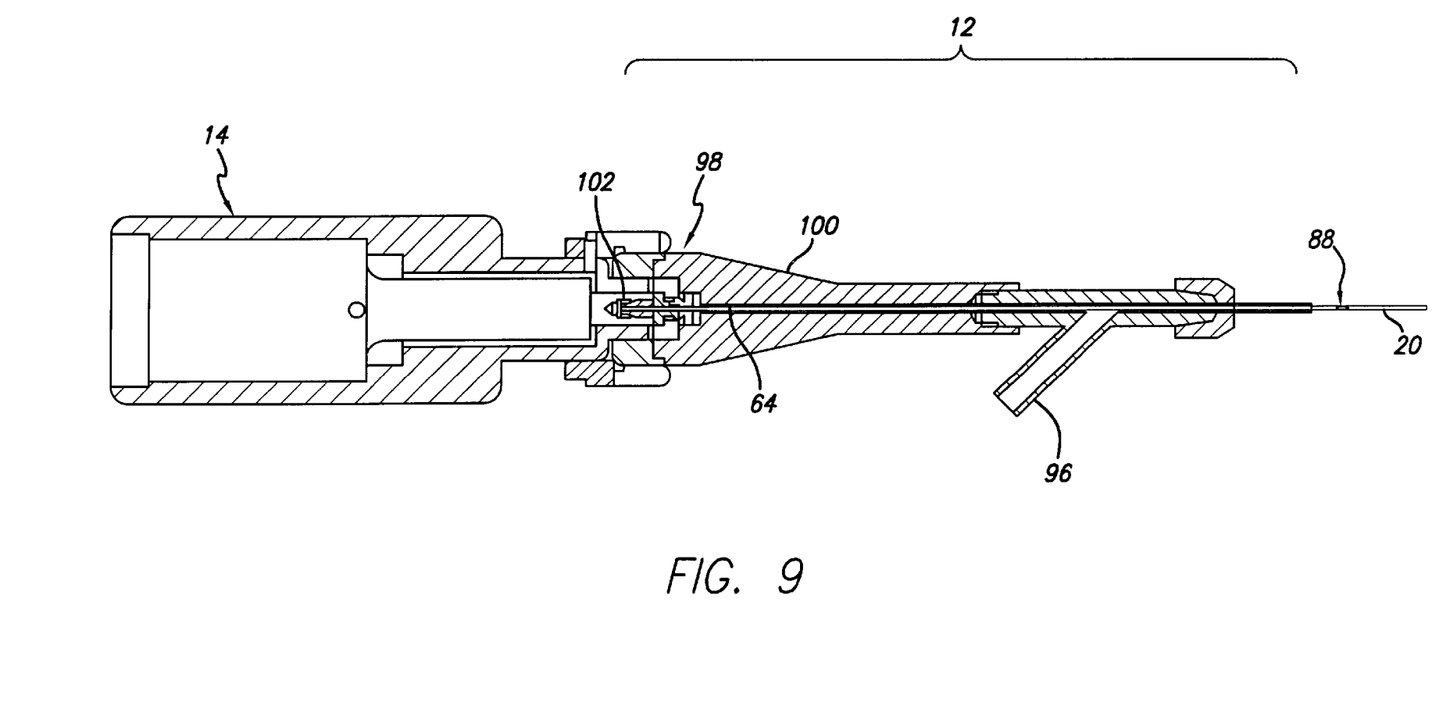
FIG. 9 is a view of a proximal catheter shaft connector assembly located at the proximal end of the catheter showing a side arm for the application of fluid and a guide wire opening or notch through which a guide wire is advanced through and retracted from the catheter shaft, the view also shows the straight-through configuration of the ultrasound transmission wire.

Various types and designs of proximal end connector assemblies 12 may be positioned on the proximal end of the catheter body 20 to facilitate operative connection of the ultrasound transmission member 64 to an ultrasound transducer 14. An example of an embodiment of such a proximal end connector assembly 12 is shown in FIG. 9. Only certain details are discussed below as connector assemblies are well known to those skilled in the art and connector assemblies other than that shown may be used.

Just distal to the connector assembly 12 but forming a part of it is a guide wire opening in the form of an elongated notch 88 in the catheter body 20. The notch 88 is configured to facilitate the insertion of a guide wire into the second lumen of the catheter body 20 and the retraction of a guide wire from the lumen. Because of its size and location, the exchange of guide wires in the catheter body is facilitated. A tubular fluid infusion side arm 96 extends outwardly from a location proximal to the notch 88 to permit the infusion of coolant fluid or other liquid into the same lumen of the catheter body as that in which the ultrasound transmission member is located. In an alternate embodiment, the side arm lumen may be connected to the other catheter lumen, such as the one in which the guide wire is disposed. A control handle 100 is located just distal to the proximal end 98 of the connector assembly 12 and this handle permits easier manipulation of the catheter body 20. It should be noted that the connector assembly 12 includes various threaded parts and O-rings operating with those parts to interconnect the parts of the assembly 12 however, these will not be reviewed in any detail here as their arrangement and function are well known to those skilled in the art.

The proximal end 98 of the connector assembly 12 includes a connection device for connecting the ultrasound transmission member 64 to an ultrasound transducer or horn 14. Various devices well known to those skilled in the art are usable for such connections and are not reviewed in detail here. Generally, the arrangement in FIG. 9 includes crimping the ultrasound transmission member 64 in a crimp screw 10 2. The crimp screw is then used to mate with a complementary thread disposed in the ultrasound transducer 14 to make positive connection for the conduction of ultrasonic energy through the ultrasound transmission member 64 to the distal end of the catheter. The sonic connector assembly or apparatus is preferably configured and constructed to permit passage of ultrasound energy through the ultrasound transmission member 64 with minimal lateral side-to-side movement of the ultrasound transmission member 64 while, at the same time, permitting unrestricted longitudinal forward/backward vibration or movement of the ultrasound transmission member 64.

Pressurized fluid, such as normal saline solution, may be infused through the side arm 96 to a point where such liquid flows out an aperture of the distal head 34. In another embodiment, separate cooling fluid lumina exist solely for the purpose of conducting cooling fluid. The distal head in this case includes fluid outflow apertures 140, although only one can be seen in FIG. 7. In this embodiment, two are formed in the distal head 34 aligned with the cooling lumina shown in FIG. 7.

During the intravascular procedure, with the catheter 10 disposed within the body vascular system, the operator may decide that a second guide wire, also provided, is more appropriate than the first guide wire for continuing the procedure. Alternatively, the operator may decide that the first guide wire needs adjustment before continuing the procedure. In these events the operator continues the procedure by removing the first guide wire from the catheter and the body vascular system. This is done by pulling on the proximal end of the first guide wire while grasping the proximal end of control handle 100 to hold it in place within the body vascular system. The first guide wire is pulled until it is removed through the notch 88 from the catheter 10.

The operator may then exchange the first guide wire with a second or subsequent guide wire by inserting the distal end of the second guide wire into the second lumen of the catheter body at the proximal end 18 of the catheter body. The second guide wire is advanced through the catheter by pushing on the second guide wire proximal end until the second guide wire distal end extends beyond the distal head.

The operator may reinsert the first guide wire 40 after appropriately adjusting it by reinserting the distal end of the first guide wire through the notch 88 into the second inner lumen at the proximal end of the catheter body. The first guide wire is advanced through the catheter 10 by pushing on the first guide wire proximal end until the first guide wire distal end extends beyond the distal head of the catheter body.

In an intravascular procedure using the catheters shown in the figures, a guiding catheter is introduced to the vascular system of a patient with a conventional Seldinger technique and is advanced to a selected position. A guide wire 40 is disposed across the damaged arterial section with the occlusion 36, or if the occlusion is too large, the guide wire is advanced into contact with the occlusion. The catheter/stent/ultrasound assembly is advanced over the guide wire 40 within the artery 32 until the stent 24 is directly across the occlusion 36. However, if the occlusion is too large, the ultrasound delivery device is advanced into contact with the occlusive material and ultrasound energy is applied to ablate a sufficient amount of occlusive material. The ultrasonic device 34 is used to ablate a passageway large enough for the balloon/stent combination to be located across the occlusion. The balloon 22 of the catheter is then expanded thereby expanding the stent 24 against the artery 32.

If ultrasound treatment of another site is desired but the guide wire is found to be unsuitable to be advanced into the subsequent site, the catheter/stent/ultrasound assembly (less the stent) may be held in position while the guide wire is exchanged. During the intravascular procedure, with the catheter 10 disposed within the body vascular system, the operator may decide that a second guide wire, also provided, is more appropriate than the first guide wire for continuing the procedure. Alternatively, the operator may decide that the first guide wire needs adjustment before continuing the procedure. In these events the operator continues the procedure by removing the first guide wire from the catheter and the body vascular system. This is done by pulling on the proximal end of the first guide wire while grasping the proximal end of the catheter body to hold it in place within the body vascular system. The first guide wire is pulled until it is removed from the catheter 10.

The operator may then exchange the first guide wire 40 with a second or subsequent guide wire by inserting the distal end of the second guide wire into the second lumen of the catheter body at the proximal end 46 of the catheter body. The second guide wire is advanced through the catheter by pushing on the second guide wire proximal end until the second guide wire distal end extends beyond the distal head.

The operator may reinsert the first guide wire after appropriately adjusting it by reinserting the distal end of the first guide wire into the second inner lumen at the proximal end of the catheter body. The first guide wire is advanced through the catheter 10 by pushing on the first guide wire proximal end until the first guide wire distal end extends beyond the distal head of the catheter body.

This method is used, for example, during ultrasonic lesion ablation procedures, wherein first lesion site is ultrasonically ablated using the ultrasonic tip. The guide wire may need exchanging or adjusting before advancing to the next lesion site. After exchanging or adjusting and reinserting the guide wire, it may be advanced beyond the catheter to and beyond a further lesion site. The catheter is then advanced along the guide wire until the ultrasonic tip is in location to ablate the further site. The further site is then ablated. This procedure is especially effective when used on chronic total occlusions which involve multiple lesion sites in continually narrower and more tortuous body lumina. In the case of chronic total occlusions this method may be employed multiple times during a single procedure.

The guide wire may be of a variety of configurations, including GVI and ultrasound type guide wires. In a typical intravascular procedure the guide wire is inserted into the vessel prior to the catheter 10. The guide wire is advanced into a distal body lumen, such as a coronary artery, until it extends beyond the site requiring the therapeutic procedure such as a lesion. The catheter is then advanced along the guide wire until the lesion removal means is in the correct position to treat the lesion. The improvement of this invention allows the exchanging of the first guide wire for a second guide wire or reformed first guide wire after the initial treatment of the lesion upon discovery that the first guide wire is not appropriate to be then advanced to further lesions.

A catheter with the elements of the invention as described allows the operator to exchange a guide wire 40 without removing the catheter 10 from the body vascular system. This ability is particularly advantageous when the invention is used to treat chronic total occlusions ("CTO's"). CTO's present multiple lesions (or occlusions) throughout the patient's coronary artery. After treating the first lesion the catheter needs to be advanced into smaller and more tortuous body lumina to treat further lesions. This may require the exchange of the currently used guide wire to a more appropriate guide wire. This invention allows the exchange of the guide wire without removing the entire catheter. This invention saves considerable time and effort which beneficially affects the health of the patient.

Although not discussed in any detail, a rapid exchange catheter, such as that shown in FIG. 2, is also usable with the other aspects of the invention described above and shown in the drawings.

Although the invention has been described herein with specific reference to presently preferred embodiments thereof, it will be appreciated by those skilled in the art that various additions, modifications, deletions and alterations may be made to such preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

What is claimed is:

1. A medical catheter system for recanalization of a tubular anatomical structure, such as a blood vessel, the catheter system comprising:
    an elongate flexible catheter body having a distal end and a proximal end;
    an ultrasonic delivery device mounted at the distal end of the catheter body;
    a dilatation balloon mounted at the distal end of the catheter body;
    a stent mounted at the distal end of the catheter body such that it may be delivered to the tubular anatomical structure by the distal end of the catheter body;
    a first lumen disposed longitudinally within the catheter body extending from the proximal end to the distal end and in fluid communication with the dilatation balloon for conducting expansion control fluid to the balloon; and
    an ultrasound transmission member extending longitudinally through the catheter body from the proximal end and mounted to the ultrasonic delivery device, the transmission member configured to transfer ultrasonic energy to the ultrasonic delivery device.

2. The catheter system of claim 1 wherein the ultrasonic delivery device comprises a distal head rigidly mounted to the distal end of the catheter body such that longitudinal and radial movement of the distal head only occurs with like movement of the distal end of the catheter body.

3. The catheter system of claim 1 further comprising a second lumen disposed longitudinally within the catheter body extending from the proximal end to the distal end, the second lumen having a size large enough to accept a guide wire extending into the catheter from the proximal end of the catheter body and to permit the extension of the guide wire distally beyond the distal end;
    whereby a guide wire may be entirely removed from the catheter body and replaced by another guide wire without removing the catheter from the anatomical structure.

4. The catheter system of claim 3 wherein the ultrasonic delivery device comprises a guide wire aperture extending completely through the distal head through which the guide wire may be located, the aperture having a size large enough so that the guide wire may be completely retracted through the distal head so that the guide wire may be exchanged with another.

5. The catheter system of claim 1 wherein the stent is mounted to the outside surface of the balloon such that expansion of the balloon into contact with the tubular anatomical structure delivers the stent into a selected location at the tubular anatomical structure.

6. The catheter system of claim 1 further comprising a radiopaque marker disposed at a selected location on the catheter body.

7. The catheter system of claim 1 further comprising a protective sheath disposed over the stent and the dilatation balloon, the sheath being movable in an axial direction to selectively uncover the stent to allow delivery of the stent to the tubular anatomical structure.

8. The catheter system of claim 1 wherein the catheter body includes a guide wire port formed in the catheter body at a location between the proximal and distal ends for locating a guide wire.

9. The catheter system of claim 1 further comprising a second lumen disposed longitudinally within the catheter body extending from the proximal end to the distal end, the second lumen having a size large enough to accept a guide wire extending into the catheter from the proximal end of the catheter body and to permit the extension of a guide wire distally beyond the distal end of the catheter;
    wherein the ultrasonic delivery device comprises a distal head rigidly mounted to the distal end of the catheter body such that longitudinal and radial movement of the distal head is not possible without like movement of the distal end of the catheter body, the distal head having a guide wire aperture aligned with the second lumen, the aperture having a size large enough so that the guide wire may be completely retracted through the distal head so that the guide wire may be exchanged with another;
    whereby a guide wire may be entirely removed from the catheter body and replaced by another guide wire without removing the catheter from the anatomical structure.

10. A medical catheter system for recanalization of a tubular anatomical structure, such as a blood vessel, the catheter system comprising:
    an elongate flexible catheter body having a distal end and a proximal end;
    a distal head rigidly mounted to the distal end of the catheter body such that longitudinal and radial movement of the distal head occurs only with like movement of the distal end of the catheter body, the distal head adapted for delivery of ultrasonic energy, the distal head comprising a guide wire aperture extending completely through the distal head through which a guide wire may be located, the aperture having a size large enough so that the guide wire may be completely retracted through the distal head;
    a dilatation balloon mounted at the distal end of the catheter body;
    a stent mounted to the outside surface of the balloon such that expansion of the balloon into contact with the tubular anatomical structure delivers the stent into a selected location at the tubular anatomical structure;
    a first lumen disposed longitudinally within the catheter body extending from the proximal end to the distal end and in fluid communication with the dilatation balloon for conducting expansion control fluid to the balloon; and
    an ultrasound transmission member extending longitudinally through the catheter body from the proximal end and mounted to the distal head, the transmission member configured to transfer ultrasonic energy to the distal head; and
    a second lumen disposed longitudinally within the catheter body extending from the proximal end to the distal end and longitudinally aligned with the guide wire aperture of the distal head, the second lumen having a size large enough to accept a guide wire extending into the catheter from the proximal end of the catheter body and to permit the extension of a guide wire distally beyond the distal head;
    whereby a guide wire may be entirely removed from the catheter body and replaced by another guide wire without removing the catheter from the anatomical structure.

11. The catheter system of claim 10 further comprising a protective sheath disposed over the stent and the dilatation balloon, the sheath being movable in an axial direction to selectively uncover the stent to allow delivery of the stent to the tubular anatomical structure.

12. The catheter system of claim 11 further comprising a radiopaque marker disposed at a selected location on the catheter body.

13. The catheter system of claim 10 wherein the catheter body includes a guide wire port formed in the catheter body at a location between the proximal and distal ends for locating a guide wire.

14. A method for recanalization of a tubular anatomical structure, such as a blood vessel, the method comprising the steps of:

advancing an elongate flexible catheter body to a lesion in the tubular anatomical structure, the catheter body having a distal end and a proximal end and an ultrasound transmission member extending longitudinally from the proximal end to an ultrasonic delivery device mounted at the distal end, the transmission member configured to transfer ultrasonic energy to the ultrasonic delivery device;

applying ultrasonic energy to the ultrasound transmission member at the proximal end of the catheter body so that the energy will be conducted to the ultrasonic delivery device;

applying ultrasonic energy to the lesion with the ultrasonic delivery device located at the distal end of the catheter body to ablate the lesion;

crossing the lesion with a guide wire;

crossing the lesion with a dilatation balloon mounted at the distal end of the catheter body;

dilating the lesion with the dilatation balloon;

delivering a stent to the dilated lesion from the distal end of the catheter body; and withdrawing the catheter from the tubular anatomical structure.

15. The method of claim 14 further comprising the steps of:

removing a first guide wire from the catheter body while retaining the catheter body in place in the tubular anatomical structure; and inserting a second guide wire through the catheter body while it remains in place in the tubular anatomical structure.

16. The method of claim 14 further comprising the step of delivering the stent to the lesion at the same time that the balloon is expanded to dilate the lesion.

17. The method of claim 14 wherein the step of applying ultrasonic energy comprises the step of applying ultrasonic energy with a distal head rigidly mounted at the distal end of the catheter body, the distal head mounted such that longitudinal and radial movement of the distal head occurs only with like movement of the distal end of the catheter body.

* * * * *

UNITED STATES PATENT AND TRADEMARK OFFICE
CERTIFICATE OF CORRECTION

PATENT NO.     : 6,461,383 B1
DATED          : October 8, 2002
INVENTOR(S)    : Douglas H. Gesswein et al.

It is certified that error appears in the above-identified patent and that said Letters Patent is hereby corrected as shown below:

Column 13,
Line 21, change "18", to read -- 46 --.

Signed and Sealed this

Twentieth Day of May, 2003

JAMES E. ROGAN
*Director of the United States Patent and Trademark Office*